(12) United States Patent
Greywall

(10) Patent No.: US 6,872,947 B1
(45) Date of Patent: Mar. 29, 2005

(54) MEMS-BASED SPECTROPHOTOMETRIC SYSTEM

(75) Inventor: Dennis S. Greywall, Whitehouse Station, NJ (US)

(73) Assignee: Lucent Technologies Inc., Murray Hill, NJ (US)

(*) Notice: Subject to any disclaimer, the term of this patent is extended or adjusted under 35 U.S.C. 154(b) by 0 days.

(21) Appl. No.: 10/667,937

(22) Filed: Sep. 22, 2003

(51) Int. Cl.$^7$ .................................................. G01J 5/02
(52) U.S. Cl. ........................... 250/339.13; 359/290
(58) Field of Search ................................ 250/372, 373, 250/338.5, 339.13, 343, 345; 359/290, 572, 566

(56) References Cited

U.S. PATENT DOCUMENTS

| | | | |
|---|---|---|---|
| 5,173,749 A | 12/1992 | Tell et al. ................. | 356/437 |
| 5,501,893 A | 3/1996 | Learmer et al. ............ | 428/161 |
| 5,512,757 A * | 4/1996 | Cederstrand et al. ....... | 250/373 |
| 5,629,790 A | 5/1997 | Neukermans et al. ....... | 359/198 |
| 5,936,250 A | 8/1999 | Baliga et al. ............... | 250/373 |
| 6,064,488 A * | 5/2000 | Brand et al. ................ | 356/440 |
| 6,201,631 B1 | 3/2001 | Greywall .................... | 359/245 |
| 6,344,648 B1 | 2/2002 | Boucher et al. ............ | 250/343 |
| 6,509,566 B1 | 1/2003 | Wamsley et al. ........ | 250/338.5 |

* cited by examiner

Primary Examiner—Hung Xuan Dang
Assistant Examiner—Tuyen Tra

(57) ABSTRACT

A portable spectrophotometric system for detecting one or more target substances. In a representative embodiment, a system of the invention has an optical grating, an array of photo-detectors, and a MEMS device having a movable plate positioned between the grating and the array. Light transmitted through a gaseous sample is dispersed by the grating and is imaged onto the movable plate, which has a plurality of openings corresponding to selected infrared absorption lines of the target substance. A small-amplitude oscillation is imparted onto the plate such that the openings periodically move in and out of alignment with the corresponding intensity features in the image, which modulates electrical signals generated by the corresponding photo-detectors. A lock-in signal processor analyzes the modulation pattern by comparing it to the pattern expected in the presence of the target substance. When a positive correlation between the patterns is established, the system warns the user about the presence of the target substance.

25 Claims, 4 Drawing Sheets

MEMS-BASED SPECTROPHOTOMETRIC SYSTEM

CROSS-REFERENCE TO RELATED APPLICATIONS

The subject matter of this application is related to that of U.S. patent application Ser. No. 10/153,294 filed on May 22, 2002 and entitled "Monolithic In-Plane Shutter Switch," the teachings of which are incorporated herein by reference.

BACKGROUND OF THE INVENTION

1. Field of the Invention

The present invention relates to sensors and, more specifically, to optical gas detectors.

2. Description of the Related Art

Gas analyzers are used in environmental monitoring, industrial process control, geologic exploration, and medical, analytical, and military applications. For example, gases such as hydrogen sulfide and sulfur dioxide accompany natural gas and are often present in industrial environments. Since exposure to these gases is a health hazard, low concentrations, typically in the range of parts per million (ppm), need to be detected.

Different analytical techniques such as optical spectroscopy, mass spectrometry, gas chromatography, electrochemical analysis, etc., may be used for detection of substances present in relatively low concentrations. One particular technique, optical spectrophotometry, is based on the absorption of electromagnetic radiation by the sample in a selected spectral range and is generally recognized to have relatively high sensitivity and speed of analysis. A spectrophotometric system typically has (i) a light source; (ii) a monochromator, which filters the light from the light source so that only a limited wavelength range is allowed to irradiate the gas sample contained in a sample cell; and (iii) a photo-detector, which measures the amount of light transmitted through the sample. Representative prior-art spectrophotometric systems operating in either ultraviolet (UV) or infrared (IR) parts of the spectrum are described, for example, in U.S. Pat. Nos. 5,936,250 and 6,344,648, the teachings of both of which are incorporated herein by reference. However, one problem with prior-art spectrophotometric systems is that they are relatively difficult to adapt for portable, particularly hand-held, applications.

SUMMARY OF THE INVENTION

Problems in the prior art are addressed, in accordance with the principles of the present invention, by a portable spectrophotometric system for detecting one or more target substances. In a representative embodiment, a system of the invention has an optical grating, an array of photo-detectors, and a MEMS device having a movable plate positioned between the grating and the array. Light transmitted through a gaseous sample is dispersed by the grating and is imaged onto the movable plate, which has a plurality of openings corresponding to selected absorption lines of the target substance. A small-amplitude oscillation is imparted onto the plate such that the openings periodically move in and out of alignment with the corresponding intensity features in the image, which modulates electrical signals generated by the corresponding photo-detectors. A lock-in signal processor analyzes the modulation pattern by comparing it to the pattern expected in the presence of the target substance. When a positive correlation between the patterns is established, the system warns the user about the presence of the target substance.

DETAILED DESCRIPTION

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

Figure 1:
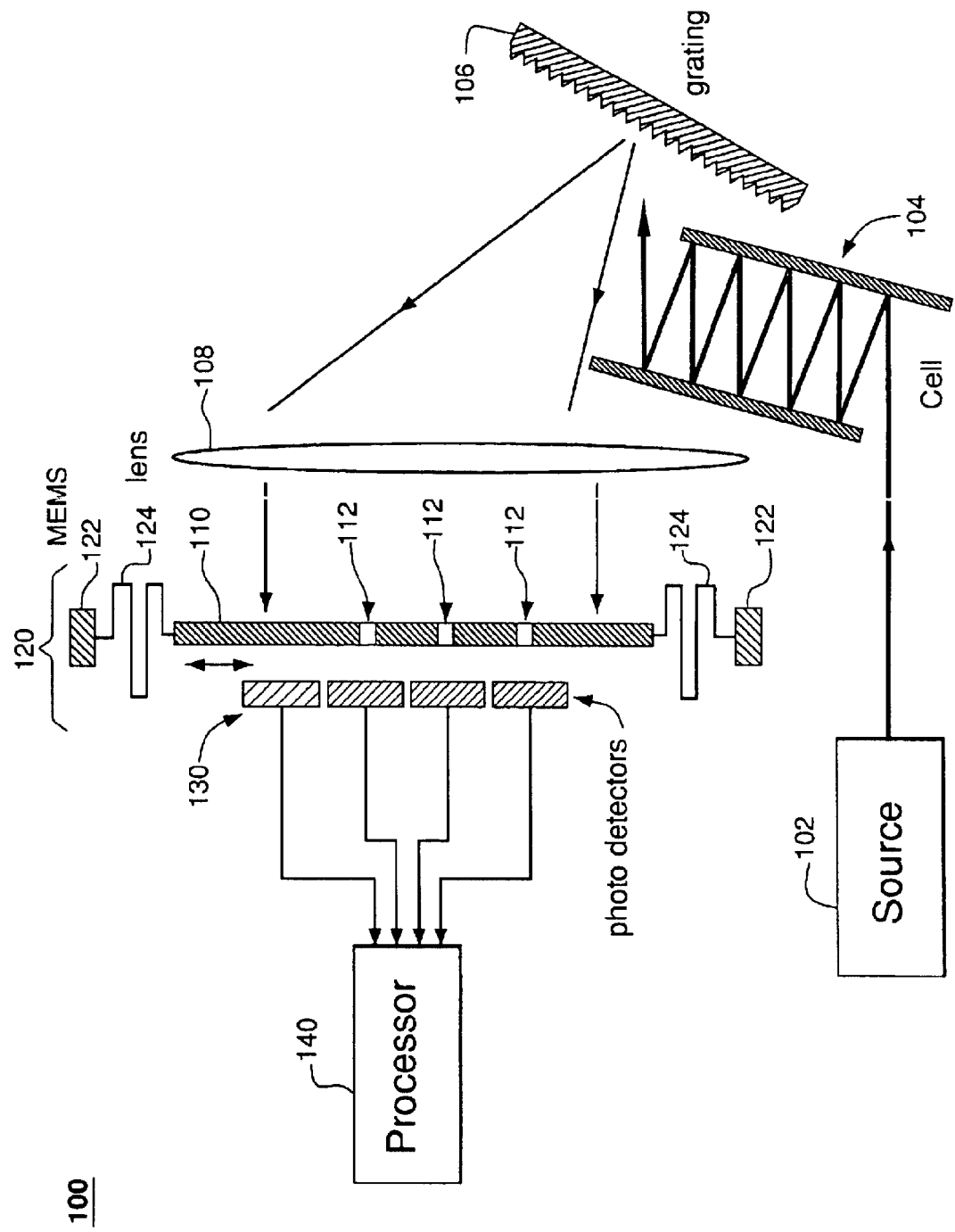
FIG. 1 shows a schematic diagram of a spectrophotometric system according to one embodiment of the present invention.

FIG. 1 shows a schematic diagram of a spectrophotometric system 100 according to one embodiment of the present invention. A beam of light generated by a broadband light source 102 is directed through a cell 104 containing a sample to be analyzed. Light transmitted through cell 104 is dispersed in wavelength by a grating 106 and is imaged by a cylindrical lens 108 onto a movable plate 110. The image produced at the surface of plate 110 is a stripe of light, in which different locations along the length of the stripe correspond to different wavelengths. Plate 110 has a plurality of openings 112 and is preferably a part of a MEMS device 120, which also includes a support structure 122 and one or more springs 124 connected between the support structure and the plate. Device 120 further includes an electrostatic actuator (not shown) adapted to controllably move plate 110 with respect to structure 122 as indicated by the double-headed arrow in FIG. 1. Plate 110 allows light to pass through openings 112 and substantially blocks the light impinging onto other portions of the plate. An array of photo-detectors 130 located behind plate 110 converts the transmitted light into electrical signals, which are then applied to a signal processor 140.

As will be further illustrated below, IR absorption of gases is typically characterized by the presence of relatively narrow absorption lines, each of which usually corresponds to a particular rotational and/or vibrational mode of the gas molecule. Each of these absorption lines produces a corresponding intensity feature in the image at plate 110. For example, a relatively strong absorption line will produce a corresponding black (i.e., having substantially no light) area at plate 110 while the areas adjacent to the black area will have a relatively high light intensity. Position of each opening 112 within plate 110 is chosen such that it can be aligned with the intensity feature corresponding to a selected absorption line of the target gas to be detected. It is also preferred that, for each target gas, plate 110 has two or more openings 112. In addition, plate 110 may have one or more openings 112 corresponding to selected strong absorption lines of air, which may be used for calibration purposes as further detailed below.

In a representative configuration, system 100 operates as follows. First, device 120 is wavelength calibrated. During calibration, the actuator of device 120 is biased to align openings 112 corresponding to absorption lines of air with the appropriate intensity features (e.g., black areas) of the image at plate 110. Proper alignment of plate 110 is achieved when the intensity profile measured by detectors 130 has the expected intensity pattern corresponding to air. Next, detection of a target gas is performed as follows. When the target gas is present in cell 104, the intensity profile measured by detectors 130, in addition to the air pattern, will also include an intensity pattern corresponding to the target gas. After calibration, openings 112 corresponding to the target gas are aligned with the corresponding intensity features (if present) in the image at plate 110 resulting from light absorption by the target gas. However, due to the unknown and possibly low concentration of the target gas, these intensity features may be relatively weak. To enable detection of weak absorption, the actuator in device 120 is configured to impart onto plate 110 a small-amplitude oscillation, e.g., in the kHz frequency range, about the equilibrium position set during the calibration. Due to the oscillation, each opening 112 corresponding to the target gas periodically moves in and out of alignment with the respective intensity feature, thereby changing in a periodic fashion the amount of light transmitted through the opening and therefore modulating the signal generated by the corresponding detector 130.

Processor 140, preferably using lock-in detection techniques, measures the appropriate ac components having a frequency corresponding to the oscillation frequency of plate 110 in the signals generated by detectors 130. To discriminate against false positives, processor 140 is preferably configured to verify correlations expected between the signals generated by different detectors 130 corresponding to the same target gas. Such correlations may include (i) simultaneous presence of the appropriate ac components and/or (ii) proper relative amplitudes of said components in accordance with relative magnitudes of the corresponding absorption lines in the absorption spectrum of the target gas. In addition, processor 140 may optionally be configured to determine the concentration of the target gas using the measured ac amplitudes.

Figure 2:
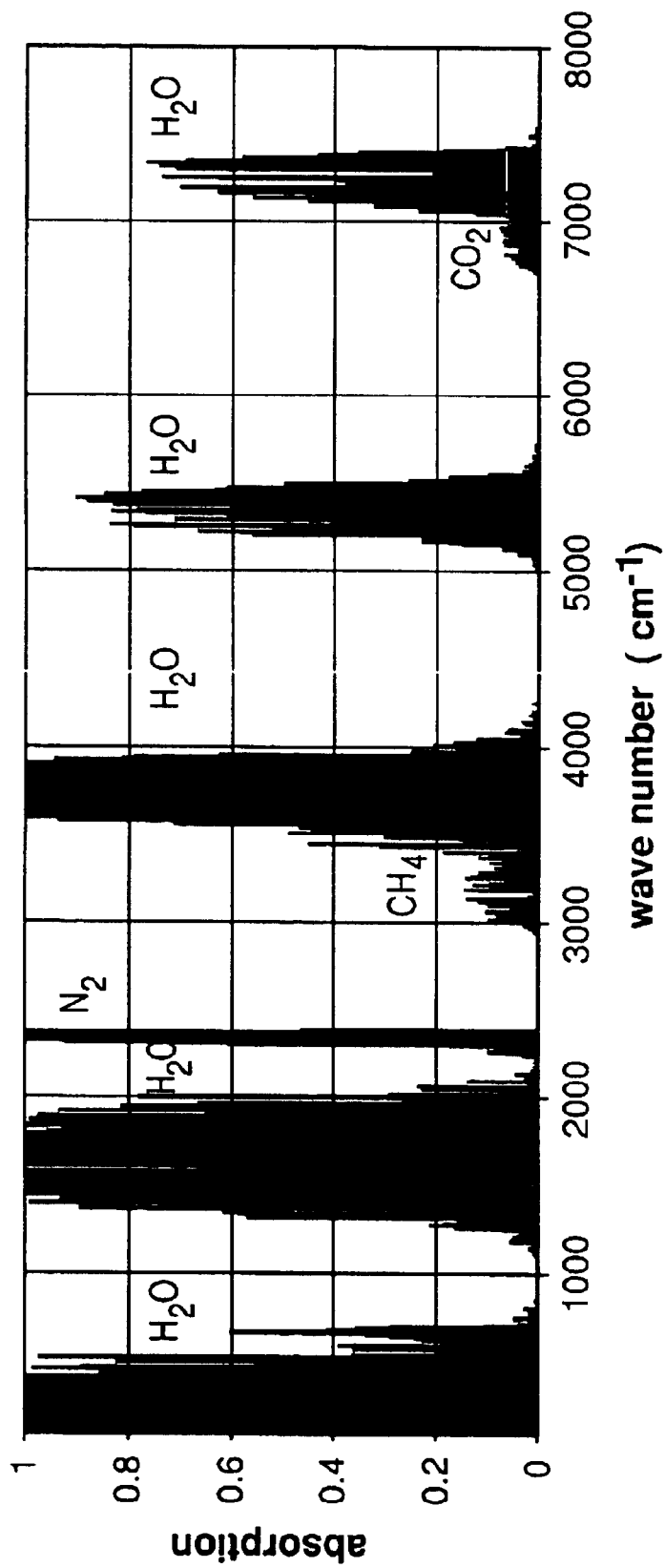
FIG. 2 graphically shows optical absorption for mean latitude summer air at pressure p=1 atm. and temperature T=296 K.
Figure 3:
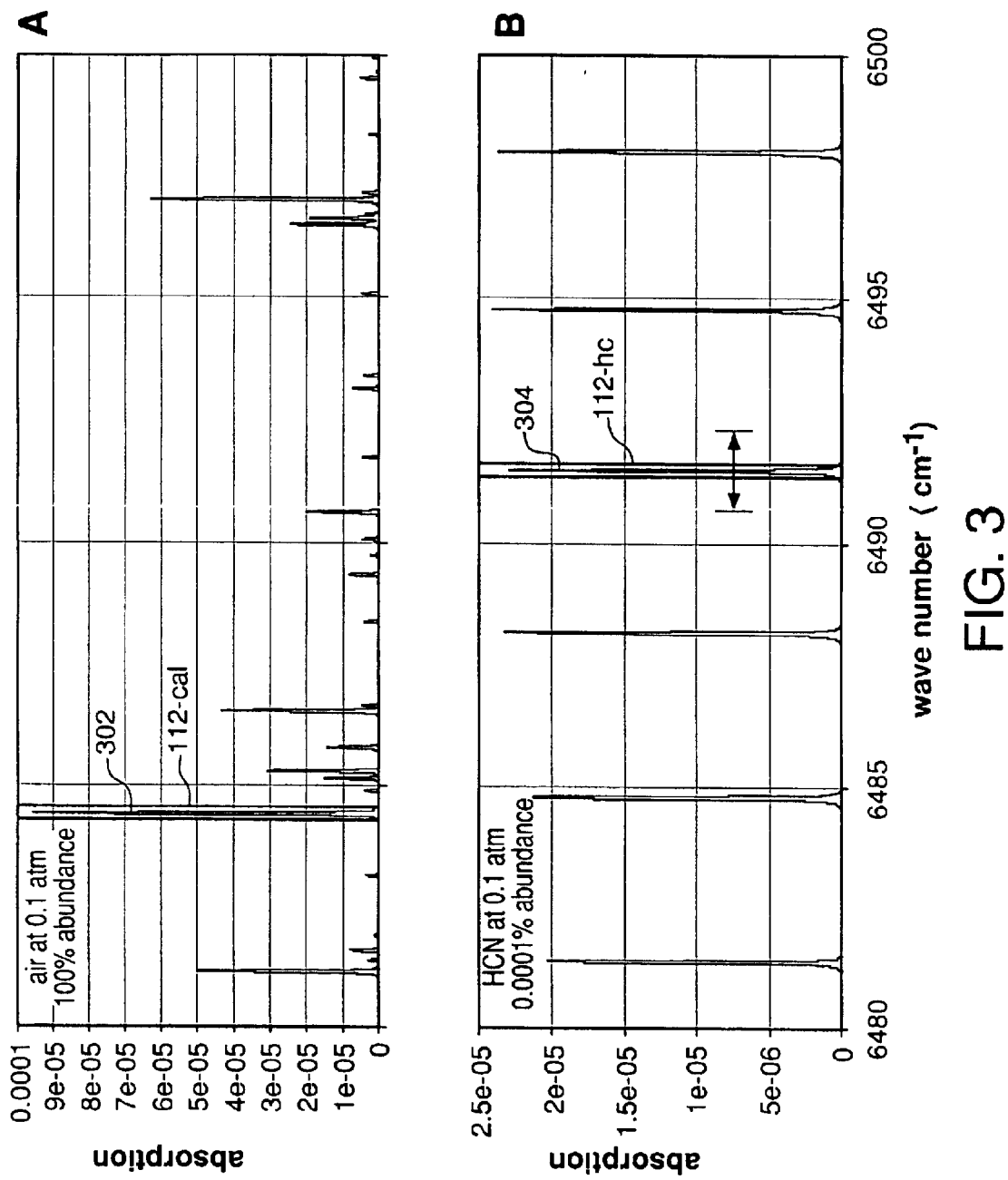
FIGS. 3A–B compare absorption spectra of air and hydrogen cyanide at p=0.1 atm. and T=296 K.

FIGS. 2 and 3 further illustrate the principle of operation of system 100 in a representative embodiment adapted for the detection of hydrogen cyanide (HCN), a highly toxic gas. More specifically, FIG. 2 graphically shows optical absorption for mean latitude summer air at pressure p=1 atm. and temperature T=296 K; and FIGS. 3A–B compare absorption spectra of air and HCN at p=0.1 atm. and T=296 K; the abundance of HCN is 1 ppm. Each value of absorption (A) shown in FIGS. 2 and 3 represents a relative amount of electromagnetic radiation that is absorbed in a gas column of length l and is expressed by the following equation:

$$A=1-\exp(-k_\lambda l) \quad (1)$$

where $k_\lambda$ is the absorption coefficient at wavelength $\lambda$.

FIG. 2 shows optical absorption for a column (l=1 m) of air having the following composition: 77.393230% of nitrogen; 20.710864% of oxygen; 1.862987% of water; 0.032701% of carbon dioxide; 0.000168% of methane; 0.000032% of nitrous oxide; 0.000015% of carbon monoxide; and 0.000003% of ozone. As indicated by the data in FIG. 2, air has certain spectral "transparency" windows (i.e., spectral regions where absorption is relatively weak), which are located between strong absorption bands of individual air components. For example, one such transparency window is between 5700 and 6600 $cm^{-1}$. One or more spectral transparency windows may be used to detect optical absorption of target gases. Alternatively, one or more relatively narrow gaps (not discernible in FIG. 2) between absorption lines composing a selected strong absorption band may similarly be used to detect optical absorption of target gases.

FIGS. 3A–B show optical absorption spectra of air and HCN, respectively, in the spectral range from 6480 to 6500 $cm^{-1}$, which is within the spectral transparency window indicated above. Referring now to FIG. 3A, in one embodiment, a spectral line 302 corresponding to water vapor is selected as a calibration feature. Accordingly, plate 110 (FIG. 1) has opening 112-cal indicated in FIG. 3A by the two vertical lines near spectral line 302. During calibration, plate 110 is positioned such that opening 112-cal aligns with line 302 as shown in FIG. 3A. Additional openings 112-cal not shown in FIG. 3A may be used to achieve and/or verify the alignment.

Referring to FIG. 3B, a spectral line 304 corresponding to HCN is selected as a signature feature of that gas. Accordingly, plate 110 (FIG. 1) has opening 112-hc indicated in FIG. 3B by the two vertical lines near spectral line 304. When opening 112-cal is aligned with line 302 as shown in FIG. 3A, opening 112-hc aligns with line 304 as shown in FIG. 3B. The horizontal double-headed arrow in FIG. 3B indicates a representative oscillation amplitude for plate 110 (FIG. 1). Due to this oscillation, the signal generated by detector 130 located behind opening 112-hc is modulated with the frequency twice the oscillation frequency. Processor 140 (FIG. 1) processes the modulated signal, measures its amplitude, and preferably verifies that this modulated signal properly correlates with other modulated signals corresponding to additional openings 112-hc (not shown in FIG. 3B). When a positive correlation is established, system 100 warns the user about the presence of HCN and optionally uses the modulation amplitudes to determine and display its concentration.

In a preferred embodiment, cell 104 is a multi-pass cell having an effective optical path length of about 1 to 10 m. A representative multi-pass cell that may be used in one embodiment of system 100 is described in U.S. Pat. No. 5,173,749, the teachings of which are incorporated herein by reference. In one embodiment, cell 104 is an airtight cell, which has valves connected to a pump (not shown in FIG. 1) configured to reduce pressure in the cell prior to or after sample injection. Optionally, cell 104 has heaters to vaporize liquid samples. In another embodiment, cell 104 has vents enabling unencumbered gas exchange with ambient air.

Figure 4:
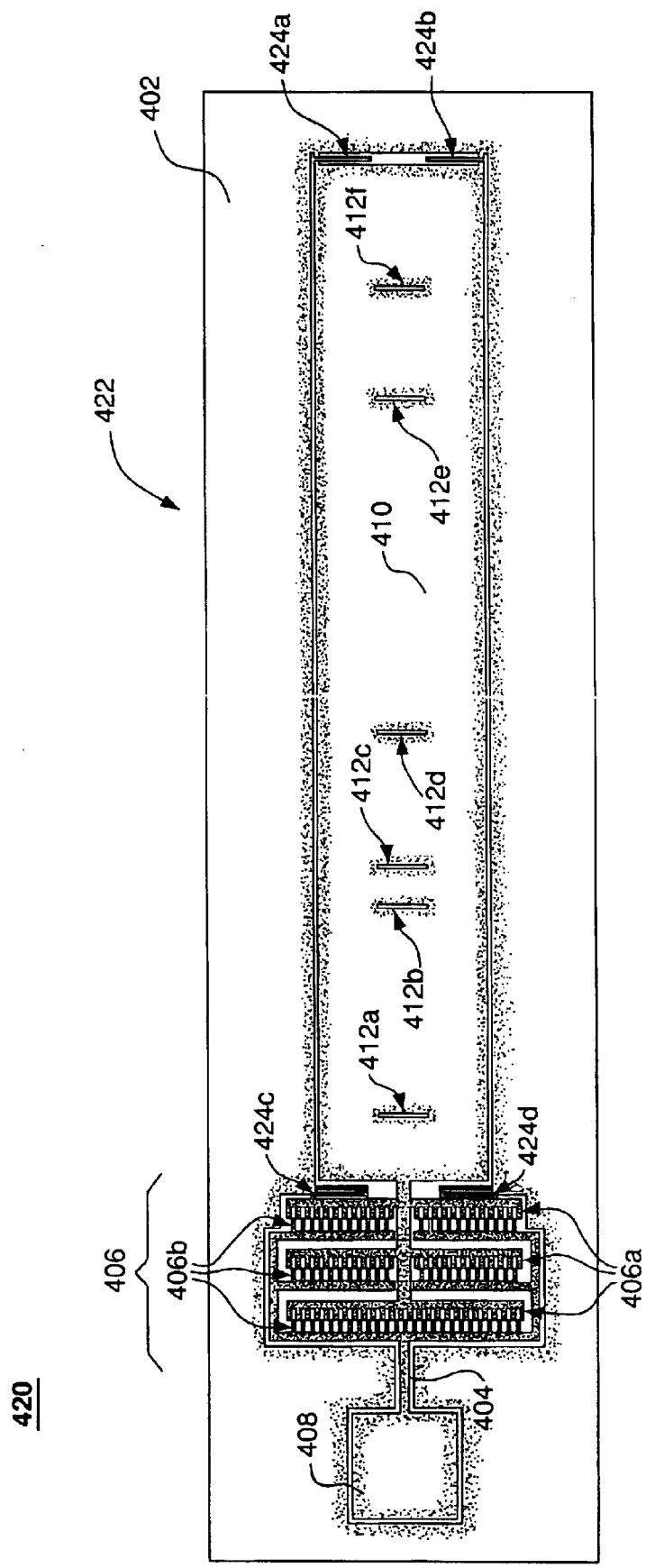
FIG. 4 shows a top view of a MEMS device that can be used in the system of FIG. 1 according to one embodiment of the present invention.

FIG. 4 shows a top view of a MEMS device 420 that can be used as MEMS device 120 according to one embodiment of the present invention. Device 420 comprises a movable plate 410 supported on a wafer 422 by four serpentine springs 424a–d. In different embodiments, a different number of springs may be used. Wafer 422 preferably comprises at least three layers: a substrate layer (not shown), an overlayer 402, and a thin insulating layer (not shown) located between the substrate layer and the overlayer. The insulating layer electrically isolates overlayer 402 from the substrate layer. Overlayer 402 and the substrate layer may be silicon and the insulating layer may be silicon oxide. Plate 410 is formed using overlayer 402 while the underlying portions of the substrate and insulating layers are removed to enable the plate mobility. Plate 410 has six slots 412a–f, two of which may be calibration slots corresponding to selected absorption lines of air and the remaining four slots may be slots corresponding to absorption lines of one or more target gases.

Device 420 further comprises a comb-drive actuator 406 including (i) a mobile portion 406a connected to plate 410 and (ii) an immobile portion 406b attached to wafer 422.

Portion 406a of actuator 406 is formed using layer 402 and is detached from the underlying substrate and insulating layers to permit in-plane motion of that portion and plate 410. Portion 406b of actuator 406 is electrically connected to a contact pad 408 using a contact track 404. Portion 406b of actuator 406, track 404, and pad 408 are electrically isolated from the rest of the device structure using the underlying insulation of the insulating layer and the surrounding grooves in overlayer 402. In contrast, portion 406a of actuator 406 is in electrical contact with overlayer 402, e.g., via springs 424c–d. Thus, a voltage differential can be applied between portions 406a–b of actuator 406. In one configuration, layer 402 may be connected to a negative terminal of a voltage source (e.g., ground), whereas pad 408 may be connected to a positive terminal of that voltage source configured to apply voltage between portions 406a–b of actuator 406. Contact pad 408 may be metal-plated as known in the art for better ohmic contact with a wire lead (not shown).

In one configuration, device 420 may be operated as follows. First, a suitable dc voltage is applied between portions 406a–b of actuator 406, e.g., as explained above, to align calibration slots 412 with the appropriate absorption lines of air. Spring force generated by deformed springs 424 counterbalances the attractive electrostatic force generated between portions 406a–b of actuator 406. Then, in addition to the dc voltage, a small ac voltage, for example, having a frequency of about 20 kHz, is applied between portions 406a–b. The ac voltage causes plate 410 to oscillate at that frequency about the position corresponding to the dc voltage. Assuming that grating 106 has 100 grooves per mm and lens 108 has a focal lens of about 50 mm, an ac voltage producing the oscillation amplitude of about 10 $\mu$m will effectively move slots 412 in and out of alignment with the corresponding absorption features of the image at plate 410.

Device 420 may be fabricated from a silicon-on-insulator (SOI wafer) using different fabrication techniques. For example, an etch fabrication method may be used. It is known that silicon etches significantly faster than silicon oxide using, e.g., reactive ion etching (RE). Similarly, silicon oxide etches significantly faster than silicon using, e.g., fluorine-based etchants. Relatively deep cavities in a relatively thick substrate layer may be defined using a standard, anisotropic etching technique, such as deep RIE. Deep RIE stops automatically at the oxide layer acting as an etch stop. Various parts of device 420 may be mapped onto the corresponding layer using lithography. Additional description of various etching steps may be found, for example, in U.S. Pat. Nos. 6,201,631, 5,629,790 and 5,501,893, the teachings of all of which are incorporated herein by reference.

Although fabrication of device 420 has been described in the context of using silicon/silicon oxide SOI wafers, other suitable materials may similarly be used. The materials may be appropriately doped as known in the art. Various surfaces may be modified, e.g., by metal deposition and/or by ion implantation. Also, differently shaped plates, actuators, and/or support structures may be implemented without departing from the scope and principle of the invention. Different embodiments may include differently shaped and/or configured springs, where the term "spring" refers in general to any suitable elastic structure that can recover its original shape after being distorted.

Advantageously, due to the relatively small size of MEMS device 420, a spectrophotometric system of the invention employing said device has a size suitable for portable applications. Further miniaturization may be achieved by implementing the signal processor (e.g., processor 140) and the array of photo-detectors (e.g., detectors 130) in a single integrated circuit. In addition, processor 140, detectors 130, and MEMS device 120 (or device 420) may be implemented as a system on a chip (SOC).

While this invention has been described with reference to illustrative embodiments, this description is not intended to be construed in a limiting sense. Although the invention was described in reference to IR light, it may also be practiced using UV light or other parts of the electromagnetic spectrum. System 100 may be designed to use spectral features other than absorption lines, e.g., an edge of a relatively wide absorption band or an emission line. For example, in one embodiment, light source 102 is a laser adapted to excite fluorescence in the sample contained in cell 104 and openings 112 correspond to selected fluorescence lines of the sample. Openings 112 may correspond to two or more target substances. Various modifications of the described embodiments, as well as other embodiments of the invention, which are apparent to persons skilled in the art to which the invention pertains are deemed to lie within the principle and scope of the invention as expressed in the following claims.

Although the steps in the following method claims, if any, are recited in a particular sequence with corresponding labeling, unless the claim recitations otherwise imply a particular sequence for implementing some or all of those steps, those steps are not necessarily intended to be limited to being implemented in that particular sequence.

What is claimed is:

1. A spectrophotometric system, comprising:
    an optical grating adapted to disperse in wavelength light received from a sample;
    one or more photo-detectors adapted to convert dispersed light into electrical signals; and
    a movable plate having one or more openings corresponding to one or more spectral features of a target substance, wherein the movable plate is located between the grating and the one or more photo-detectors and is adapted to pass light through said one or more openings to said photo-detectors.

2. The system of claim 1, wherein the movable plate is adapted to oscillate about a selected position to vary amount of light passed through the openings.

3. The system of claim 1, wherein, for each opening in the movable plate, the system has at least one photo-detector.

4. The system of claim 1, further comprising a cell containing the sample.

5. The system of claim 1, further comprising:
    a light source adapted to irradiate the sample; and
    a lens adapted to image the light received from the sample onto the movable plate.

6. The system of claim 1, wherein the system is adapted to operate using infrared light.

7. The system of claim 1, further comprising a signal processor adapted to perform correlation processing of electrical signals generated by different detectors to determine presence of the target substance in the sample.

8. The system of claim 7, wherein:
    the movable plate is adapted to oscillate about a selected position to vary amount of light passed through the openings; and
    the processor is adapted to use lock-in processing to measure one or more ac components of the electrical signals, said ac components corresponding to the plate oscillation.

9. The system of claim 1, wherein the movable plate is a part of a MEMS device.

10. The system of claim 9, wherein the MEMS device includes a stationary support structure and one or more springs attached between the plate and the support structure.

11. The system of claim 10, wherein the MEMS device further includes an electrostatic actuator adapted to move the plate relative to the stationary support structure in response to an electrical signal applied to the actuator.

12. The system of claim 9, wherein the MEMS device is fabricated in a planar wafer and the plate is adapted to move parallel to the plane of the wafer.

13. The system of claim 1, wherein the plate has one or more openings corresponding to one or more spectral features of air.

14. The system of claim 1, wherein the plate has openings corresponding to spectral features of a plurality of target substances, wherein a first set of one or more openings corresponds to a first target substance and a second set of one or more openings different from the first set corresponds to a second target substance different from the first target substance.

15. The system of claim 1, wherein at least one opening corresponds to an absorption line of the target substance.

16. A method for detecting a target substance, comprising:
dispersing in wavelength light received from a sample;
imaging dispersed light onto a movable plate having one or more openings corresponding to one or more spectral features of the target substance; and
measuring light passing through the one or more openings using one or more photo-detectors.

17. The method of claim 16, wherein the movable plate oscillates about a selected position to vary amount of light passing through said openings.

18. The method of claim 17, wherein the plate has one or more openings corresponding to one or more spectral features of air and, when the plate is in the selected position, each of the one or more openings corresponding to air is aligned with a corresponding intensity feature in the dispersed light.

19. The method of claim 17, further comprising applying lock-in processing to measure one or more ac components in electrical signals generated by the one or more photo-detectors, said ac components corresponding to the plate oscillation.

20. The method of claim 19, further comprising performing correlation processing of the ac components to detect the target substance.

21. The method of claim 16, wherein the movable plate is a part of a MEMS device including a stationary support structure and one or more springs attached between the plate and the support structure.

22. The method of claim 21, wherein the MEMS device further includes an electrostatic actuator adapted to move the plate relative to the stationary support structure in response to an electrical signal applied to the actuator.

23. The method of claim 21, wherein the MEMS device is fabricated in a planar wafer and the plate is adapted to move parallel to the plane of the water.

24. The method of claim 16, wherein the plate has openings corresponding to spectral features of a plurality of target substances, wherein a first set of one or more openings corresponds to a first target substance and a second set of one or more openings different from the first set corresponds to a second target substance different from the first target substance.

25. A system for detecting a target substance, comprising:
means for dispersing in wavelength light received from a sample;
means for imaging dispersed light onto a movable plate having one or more openings corresponding to one or more spectral features of the target substance; and
means for measuring light passing through the one or more openings.

* * * * *